United States Patent [19]

Schumacher et al.

[11] Patent Number: 4,534,362
[45] Date of Patent: Aug. 13, 1985

[54] METHOD AND APPARATUS FOR DETECTION OF FERTILITY

[75] Inventors: Gebhard F. B. A. Schumacher, Homewood; Stephen J. Usala, Chicago, both of Ill.

[73] Assignee: University Patents, Inc., Westport, Conn.

[21] Appl. No.: 375,883

[22] Filed: May 7, 1982

[51] Int. Cl.³ .............................................. A61B 10/00
[52] U.S. Cl. ................................... 128/738; 128/749; 604/55
[58] Field of Search ............... 128/635, 738, 749, 752, 128/759-760, 763, 765-766, 771; 604/22, 27, 35-36, 38, 54-55, 104, 118-119, 121, 164, 168, 174, 187, 207, 260, 268, 279, 330

[56] References Cited

U.S. PATENT DOCUMENTS

| | | | |
|---|---|---|---|
| 2,927,463 | 3/1960 | Stubbs | 128/738 X |
| 3,117,569 | 1/1964 | Wegner | 128/738 X |
| 3,777,743 | 12/1973 | Binard et al. | 128/749 |
| 3,796,211 | 3/1974 | Kohl | 604/55 X |
| 3,926,037 | 12/1975 | Kopito et al. | 73/53 |
| 3,961,620 | 6/1976 | Schack et al. | 128/757 |
| 3,979,945 | 9/1976 | Kopito et al. | 73/60 |
| 3,986,494 | 10/1976 | Preti et al. | 128/738 |
| 3,995,618 | 12/1976 | Kingsley et al. | 128/759 |
| 3,998,210 | 12/1976 | Nosari | 128/771 X |
| 4,002,056 | 1/1977 | Kopito et al. | 73/53 |
| 4,013,066 | 3/1977 | Schuster | 128/738 |
| 4,036,212 | 7/1977 | Karuhn | 128/2 R |
| 4,119,089 | 10/1978 | Preti et al. | 436/65 |
| 4,131,112 | 12/1978 | Kopito et al. | 128/765 |
| 4,151,833 | 5/1979 | Polishuk | 128/738 |
| 4,164,212 | 8/1979 | Schuster | 128/759 |
| 4,221,567 | 9/1980 | Clark et al. | 128/635 X |
| 4,318,414 | 3/1982 | Schuster et al. | 604/55 X |
| 4,393,879 | 7/1983 | Milgrom | 604/119 X |
| 4,396,022 | 8/1983 | Marx | 128/758 |

FOREIGN PATENT DOCUMENTS

WO82/01824 6/1982 PCT Int'l. Appl. .

OTHER PUBLICATIONS

Hilgers et al., *Ob/Gyn*, 52, 575-582, (1978).
Moghissi, K. S., *Fertil. Steril.*, 34, 89-98 (1980).
Schumacher, G. B. F., "Humoral Immune Factors in the Female Reproductive Tract and Their Changes During the Cycle", *Immunological Aspects of Infertility and Fertility Regulation*, Dhindsa/Schumacher, eds., pp. 93-141 (Elsevier North Holland, Inc., 1980).
Wilson, M. A., *The Ovulation Method of Birth Regulation*, Van Nostrand Reinhold Co., N.Y., 1980.
World Health Organization, "A Prospective Multicentre Trial of the Ovulation Method of Natural Family Planning, II, The Effectiveness Phase", *Fertil. Steril.*, 36, 591-598, (1981).
Yen, S. S. C., and R. B. Jaffe, *Reproductive Endocrinology*, Philadelphia: Saunders, 1978, pp. 126-151.
Hafez, "Histology and Microstructure of the Cervical Epithelial Secretory System", from *Cervical Mucus in Human Reproduction* (Elstein, et al., eds.), Scriptor, Copenhagen (1973); World Health Organization Colloquium, Geneva, 1972, pp. 23-32.
Moghissi, "Vaginal Fluid Constituents", from *The Biology of the Fluids of the Female Genital Tract* (Beller, et al., Eds.), Elsevier/North Holland, Inc., New York (1979), pp. 13-23.
Morishita, et al., *Gynecol. Obstet. Invest.*, 10: 157-162 (1979).

(List continued on next page.)

*Primary Examiner*—Lee S. Cohen
*Assistant Examiner*—Angela D. Sykes
*Attorney, Agent, or Firm*—Marshall, O'Toole, Gerstein, Murray & Bicknell

[57] ABSTRACT

Method and apparatus for detecting the fertile and infertile phases of the human female menstrual cycle based upon observation of cyclic volumetric and gravimetric changes in cervico-vaginal fluid.

41 Claims, 8 Drawing Figures

OTHER PUBLICATIONS

Dusitsin, et al., "Histidine in Human Vaginal Fluid", *Obstet. & Gynecol.*, 29(1): 125-129 (1967).

Viergiver, et al., "Measurement of the Cyclic Variations in the Quantity of Cervical Mucus and Its Correlation with Basal Temperature", *Am. J. Obstet. Gynecol.*, 48: 321-328 (1944).

Viergiver, et al., "Cyclic Variations in the Viscosity of Cervical Mucus and its Correlation with Amount of Secretion and Basal Temperature", *Am. J. Obstet. Gynecol.*, 51: 192-200 (1946).

Wagner, "Vaginal Transudation", in *The Biology of the Fluids of the Female Genital Tract* (Beller, et al., eds.), Elsevier/North Holland, Inc., New York (1979), pp. 25-34.

"Volumetric Self-Sampling of Cervico-Vaginal Fluid: A New Approach to Ovulation Timing", in *Fertility and Sterility*, vol. 39, pp. 304-309 (Mar. 1983), The American Fertility Society, Birmingham, Ala., publishers.

METHOD AND APPARATUS FOR DETECTION OF FERTILITY

BACKGROUND OF THE INVENTION

The present invention relates generally to the field of detecting the onset of ovulation in the human female based upon the evaluation of peripheral changes preceding, coinciding with, and succeeding the ovulatory process. More specifically, it relates to a method and associated apparatus for estimating the period of peak fertility in the human menstrual cycle for the purposes of natural contraceptive practice and fertility enhancement, by observing cyclic changes in daily quantities of cervico-vaginal fluid which accumulates naturally in the vagina.

Because of cultural or religious beliefs in certain populations and increased dissatisfaction with adverse side effects and inconvenience of hormonal, chemical or mechanical and other contraceptive methods, there is considerable present interest in a simple, practical, convenient, reliable, and effective method of birth control using natural, non-invasive techniques. Additionally, the ability to accurately detect the time of ovulation is critical where conception is desired, since after ovulation the ovum remains viable for fertilization for approximately 12-24 hours. A simple method for determining the onset of ovulation, therefore, is desirable also for fertility enhancement.

Over the past two decades there has been much research to develop techniques of ovulation timing and associated apparatus for birth control and fertility enhancement purposes. The occurrence of ovulation can be detected with some accuracy through various state of the art methods. At present these methods can give a reasonably good indication that ovulation has occurred or is imminent. However, each of these methods is subject to certain disadvantages which effect either its practicality or its reliability as a method which can be conveniently used and accurately interpreted by female subjects without medical aid and/or highly sophisticated laboratory methods.

One clinical technique suggested as a method of detecting the time of ovulation relies on a woman's ability to detect some degree of pelvic discomfort at midcycle, the time of expected ovulation. Distention of the ovary or peritoneal irritation as a result of follicular rupture are the probable causes of this "mittelschmerz." Unfortunately, because most patients do not experience or cannot reliably identify monthly "mittelschmerz," it is not a widely applicable or reliable method to detect ovulation.

For years the physical properties of cervical mucus have been used by clinicians to roughly establish the fertile period. Recently Hilgers, et al. *Ob/Gyn,* 52, 575-582, (1978) have confirmed that ovulation occurs from 3 days before to 3 days after the last day of cervical mucus symptoms (copious mucus flow, ferning, spinnbarkeit, and minimum viscoelasticity). Cervical mucus is a hydrogel secreted in the cervical portion of the uterus which, for purposes of clinical examination, must be removed from the mouth of the cervix with specially designed instruments by medical personnel. A woman cannot obtain cervical mucus by self-use of such methods or devices. See U.S. Pat. Nos. 3,926,037; 4,002,056; 4,013,066; 3,979,945.

Self-observation of the color or viscoelasticity of a mucoid vaginal discharge (cervical mucus plus vaginal discharges) to detect ovulation has also been advocated as a method of birth control. Wilson, M.A., *The Ovulation Method of Birth Regulation,* Van Nostrand Reinhold Co., N.Y. 1980. In its present form this method of birth control, called the "Ovulation" or "Billings" Method, is entirely qualitative and subjective, depending upon a woman's ability to perceive the characteristic appearance of a midcycle mucoid discharge at the opening of the vagina. The method is complicated by the fact that some women are scant cervical mucus and vaginal fluid producers, even at ovulation, making identification of mucus symptoms difficult. Some studies using this method of fertility regulation for birth control purposes have shown a failure rate of approximately 25%. [Moghissi, K. S., *Fertil. Steril.,* 34, 89, (1980); World Health Organization, "A Prospective Multicentre Trial of the Ovulation Method of Natural Family Planning. II. The Effectiveness Phase," *Fertil. Steril.,* 36, 591, (1981).]

Perhaps the presently most popular and widely used method of detecting ovulation is the graphic recording of the waking temperature at basal conditions. A significant rise in Basal Body Temperature (BBT) normally occurs 1-2 days after ovulation. Three consecutive BBT readings should be at least 0.2° C. (approximately 0.36° F) higher than the previous six daily temperatures in order to establish the infertile period. (Moghissi, K. S., *Fertil.Steril.,* 34, 89, 1980). There are several drawbacks to this method. Only basal conditions can be used; that is, a female subject must get 6-8 hours of sleep and must take her temperature immediately on awakening. Physical activity and/or alcohol consumption the night before or intermittent infections can result in spurious temperatures. A very important consideration is that BBT measurements do not indicate when ovulation is approaching, but rather provide evidence of ovulation 2 or 3 days *after* it has occurred. Additionally, many times a BBT chart can be difficult for a woman to interpret accurately.

Many other attempts to detect ovulation involve biochemical and histological evaluations of epithelial or endometrial samples, and the monitoring of hormone levels in the blood, all of which require medical expertise and sophisticated equipment and therefore are unsuited for self-use.

Several attempts to discover a simple method for self-detection of the fertile, ovulatory phase are reflected in U.S. patents. Preti, et al., U.S. Pat. No. 4,119,089 suggests a method of predicting and determining the time of ovulation by monitoring the concentration of volatile sulfur-containing compounds present in mouth air, using gas chromatography, a technique not practical for home use.

A more recent technique developed for self-use is described in Polishuk U.S. Pat. No. 4,151,833. This method teaches the detection of ovulation by measuring the water content in the vaginal cavity, using a pellet made of a hydrophilic polymer. Practice of this method involves insertion of the pellet into the vagina for approximately 8 hours every day and measurement of the pellet diameter to detect an increase in water content of cervical mucus, allegedly indicative of onset of ovulation. This method has practical disadvantages for the woman involved, including discomfort and interference with sexual activity while the pellet is in place. More importantly, the method also suffers from several interpretive disadvantages.

Cervical mucus is a hydrogel from which it is difficult to extract water. Additionally, the contents of the vagina include particulate matter, i.e., epithelial cells, bacteria, gelatinous glycoprotein strands (from cervical mucus), etc., as well as water containing serum transudate. Since much human tissue, including vaginal tissue, is 90% water, there is no way of determining what water content the pellet method is measuring during prolonged exposure of the hydrophilic pellet material to the vaginal environment. The swelling of the pellet represents the uptake of water over a long period of time during which the pellet may itself be interfering with the water equilibrium of the vaginal tissue. Any changes in water correlated with the menstrual cycle would tend to be obscured by the large total volume of water necessarily absorbed over approximately 8 hours. Furthermore, the probability of inaccuracy is great because the swelling of the pellet can only be measured by an increase in diameter; in addition, the swelling is a function of the absorbent capacity of the polymer. All of these disadvantages demonstrate the inadequacy of this method in providing a reliable and accurate means of self-detection of ovulation.

Despite the wealth of prior techniques described for ovulation detection, therefore, there remains a need for a method which is simple and reliable in both application and interpretation for self-detection of the fertile period of the human menstrual cycle.

BRIEF SUMMARY

The present invention relates to a method and apparatus for detecting the fertile and infertile phases of the human menstrual cycle, based on cyclic changes in the cervico-vaginal fluid which occur during said cycle. As used hereafter, the term "cervico-vaginal fluid" describes a fluid in the human vagina consisting of mucinous secretions from the uterine cervix and of transudate from the vaginal wall containing exfoliated vaginal cells, bacteria, white blood cells and endocervical cells.

The method of the present invention is designed for self-use by a woman and requires no medical assistance in interpretation. Practice of the method involves daily collection of cervico-vaginal fluid from the anatomic region of the upper vagina (posterior fornix) adjacent to the cervix, by means of a syringe-like aspirator. Collection is performed only once a day and represents a collection of the cervico-vaginal fluid that has accumulated in a 24-hour interval. This collection procedure is denoted "sampling". The amount of fluid obtained from this sampling procedure is recorded by volume or weight (denoted "sample volume" or "sample weight"), thus enabling a woman over a period of consecutive days to note a characteristic pattern in the recordings reliably correlated with the follicular (pre-ovulatory), ovulatory, and luteal (post-ovulatory) phases of the menstrual cycle.

Practice of the method enables a woman to observe a low average sample volume or weight of cervico-vaginal fluid during the early follicular phase, the infertile phase following menses. As ovulation approaches, the sample volume or weight of cervico-vaginal fluid noticeably increases. Two to three days prior to ovulation, or at ovulation, a peak in sample volume/weight occurs, signifying the time of optimum fertility. Advance into the luteal infertile phase is indicated by a decrease in sample volume/weight of cervico-vaginal fluid, which establishes another low average. By observing the above changes, a woman can monitor her phases of fertility and infertility for use in both contraception or conception.

The present invention also comprises an aspirator for collection of cervico-vaginal fluid, which is desirably calibrated for easy volumetric quantitation. This aspirator is designed to collect fluid from the posterior fornix of the vagina close to the cervix and prevent perforation of vaginal or cervical tissue, and is therefore simple and painless to operate. In its preferred form, the aspirator is sterilely packaged and disposable after one use. While the cervico-vaginal fluid in this device may be disposed of once the measurement has been recorded, the fluid may alternatively be transferred into a test tube for chemical analysis by medical personnel should the need for such analysis arise. Furthermore, the aspirator will desirably be formed of a clear material enabling observation of the color, translucency and consistency of the cervico-vaginal fluid, which qualities are additional means for determining phases of fertility and infertility.

The method and apparatus of the present invention may also be used in conjunction with other ovulation-detecting methods such as Basal Body Temperature to increase their accuracy.

Other aspects and advantages of the present invention will become apparent upon consideration of the following description.

DETAILED DESCRIPTION OF THE INVENTION

The method of the present invention is based on an objective and easily measurable phenomenon resulting from reproductive endocrinology and physiology.

The phase of the menstrual cycle beginning with menses is the follicular or proliferative stage in which hormonal signals from the hypothalamus stimulate the anterior pituitary gland to release follicle stimulating hormone (FSH). Under the influence of FSH, follicles in the ovary grow and secrete estrogen, which causes proliferative changes in the uterus and vagina. Toward midcycle the serum estrogen level reaches its peak approximately one day before the peak of LH (luteinizing hormone released by the pituitary gland), which causes the follicle to burst within some 16-24 hours, releasing the mature ovum (ovulation). Following ovulation the ruptured follicle develops into the corpus luteum which secretes progesterone, resulting in increasing serum levels of this hormone. In the event conception did not occur, progesterone production begins to fall off after approximately one week and menses occurs several days later. (Yen, S. S. C., and R. B. Jaffe, *Reproductive Endocrinology*, Philadelphia: Saunders, 1978,pp. 126–151).

There is a dramatic increase in cervical mucus produced by the cervix in response to estrogens, and a sharp decrease in cervical mucus production following ovulation and luteal phase production of progesterone. The mucus mixes with fluid present in the vagina and forms a pool of cervico-vaginal secretions. It is so far unknown to what extent estrogen and progesterone affect the contribution of the vaginal wall to this fluid. The hitherto unrealized concept which underlies the present invention is that volumetric or gravimetric collection or "sampling38 of cervico-vaginal secretions, in contradistinction to direct aspiration of cervical secretions from the endocervical canal, gives an excellent barometer of the fertile and infertile phases of the female menstrual cycle. The volume and weight of cervico-vaginal fluid samples obtained daily during the course of a cycle follow a distinctive pattern that is reliably correlated with the follicular (preovulatory), ovulatory, and luteal phases of the menstrual cycle.

In the early follicular phase, low levels of estrogen are associated with an average sample volume/weight of cervico-vaginal fluid, of generally no more than 100 $\mu l$ (microliter) to 200 $\mu l$. As ovulation approaches there is a noticeable increase in the sample volume/weight of the cervico-vaginal fluid. A few days prior to or at the time of presumptive ovulation when the estrogen level is highest, there is a peak sample volume/sample weight-denoted Volume Peak/Weight Peak— that is 3 to 40 fold greater than the sample volumes/weights obtained during the early follicular phase. The cervico-vaginal fluid near or at the time of the Volume/Weight Peak is remarkable not only for the relatively high magnitude of sample volume/weight, but also for a certain translucency and slimy appearance of varying degrees.

Optimal conditions for conception exist most likely one to two days after the Volume/Weight Peak. After the Volume/Weight Peak, the sample volumes/weights steadily decrease and fall to values less than $\frac{1}{3}$ of the Volume/Weight Peak. During the latter period these samples of cervico-vaginal secretions show not only low volume/weight but also a pasty, white consistency and minimal or no slimy appearance. Two consecutive days of low sample volume/weight less than approximately $\frac{1}{3}$ Volume/Weight Peak establish the transition from fertile to infertile phase.

Thus, practice of the method of the present invention involves self-collection (sampling) of cervico-vaginal fluid from the vaginal cavity and observation of the volumetric or gravimetric pattern formed by recording the sample volume or sample weight of cervico-vaginal fluid over a course of days. Preferably, collection of cervico-vaginal fluid each day following menses is desirable for a woman to recognize the low average sample volume/weight or baseline characteristic of the early follicular (infertile) phase. However, the method is effective when collection is performed at least several days prior to, during, and following projected ovulation. It is desirable in the practice of the method that collection of cervico-vaginal fluid sample occur at approximately the same time each day, preferably upon waking. However, the pattern of volumetric and gravimetric changes detectable by practice of the method is distinct and noticeable when the daily collection is performed at any time during the day, even when the interval between collections is somewhat greater or lesser than 24 hours. Intercourse six to eight hours before collection will not disrupt the predictive ability of the method. Even in the event of intercourse close to the time of sampling, the presence of semen in the cervicovaginal fluid would at most give a false high reading, indicating that the woman could be approaching ovulation and should refrain from unprotected intercourse if using the method for birth control.

When the method is utilized for natural family planning, unprotected intercourse should be avoided from the beginning of the sample volume/weight increase or from the day calculated from the "21 day Rule" (21 subtracted from the shortest cycle length in the preceding 6 months). After the transition to the infertile luteal phase, two days after the second consecutive day of low sample volume/weight after the Volume/Weight Peak, unprotected intercourse may then be resumed. This time period takes into consideration a three to four day survival time of spermatozoa as well as the time span of possible ovulation.

When the method is used to promote conception, the converse applies. Intercourse should take place during the day of Volume/Weight Peak or the day after, presumably the time of optimal fertility.

Figure 4:
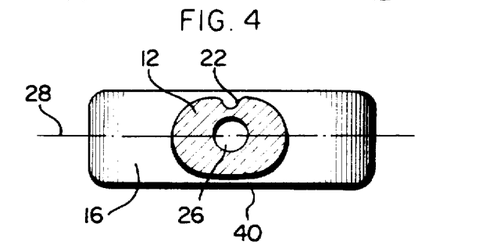
FIG. 4 is a transverse frontal view of the aspirator taken along line 4—4 in FIG. 2, along the longitudinal plane of the face of the mouth means.
Figure 5:
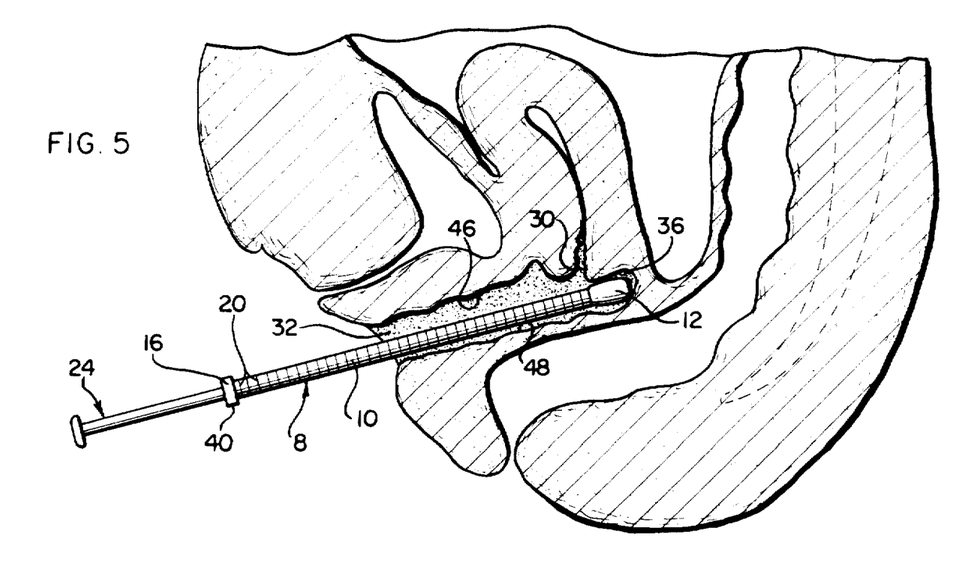
FIG. 5 is an anatomical view demonstrating proper positioning of the aspirator of the present invention.

Further description of the method is contained in the following description of the cervico-vaginal fluid aspirator of the present invention. While the detail of the apparatus is contained in FIGS. 1 through 4, all references to operation of the apparatus and its relation to anatomical tissues and organs are illustrated in FIG. 5.

Figures 1, 2:
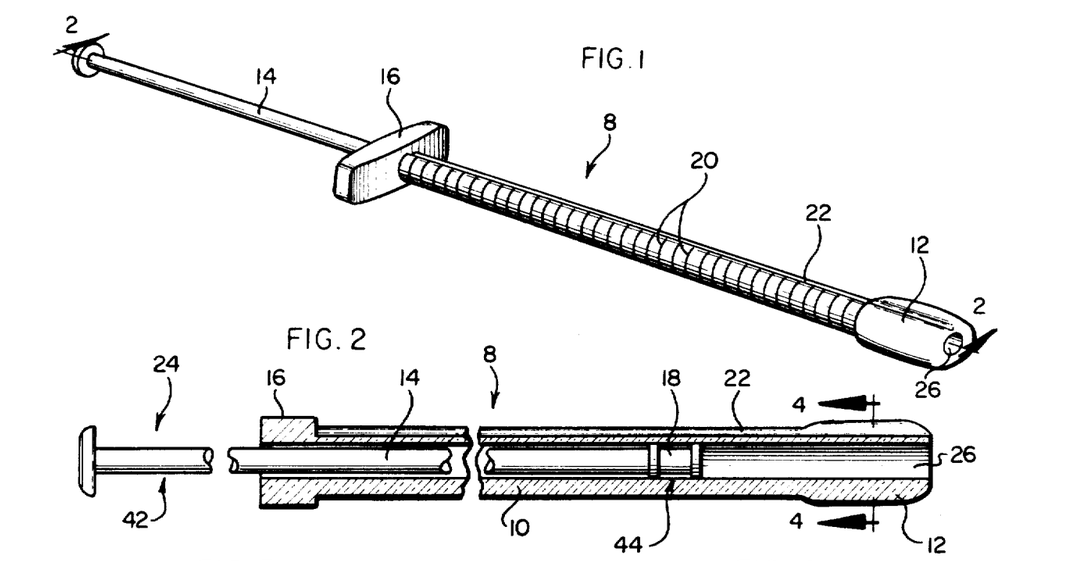
FIG. 1 is a perspective view of a cervico-vaginal fluid aspirator according to the invention.
FIG. 2 is a cross-sectional view taken along line 2—2 in FIG. 1.
Figure 3:
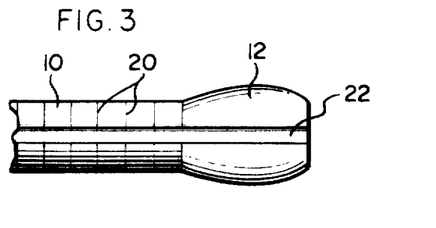
FIG. 3 is a magnified view of the mouth means and a portion of the tube means of the aspirator.

Indicated generally at 8 in FIG. 1 is a cervico-vaginal fluid aspirator according to the present invention. The aspirator 8 comprises an elongated cylindrical tube 10 having a continuous passage 26 therethrough terminating at one end in a mouth 12. The tube 10 is desirably a length sufficient to allow the mouth 12 to lie in the posterior fornix 36 (FIG. 5) when the aspirator 8 is fully inserted. Additionally, the length of tube 10 enables the manipulation of the fluid in the tube 10 for removal of air bubbles and accurate measurement. The mouth 12 is a bulbous (bulbheaded) enlargement of tube 10, shown most clearly in the enlarged view of FIG. 3, for preventing traumatization or perforation of the tissue of the vagina 32 or the cervix 30 during use of the aspirator 8. The bulbous mouth 12 has an elliptical frontal shape as shown in FIG. 4 to ease its slipping into the posterior fornix 36 of the vagina 32, beneath the cervix 30 (FIG. 5).

Guide 16 for maintaining the mouth 12 of the aspirator 8 in the most desirable position upon insertion into the vagina 32 is positioned at the end of tube 10 opposite the mouth 12. The guide 16 is oriented with the elliptical face of the mouth 12 so that the longitudinal axis 28 of the elliptical frontal face of the mouth 12 is parallel with the longest side 40 of the rectangular guide 16. This preferred orientation is seen most clearly in FIG. 4. The orientation of the guide 16 with the mouth 12 enables proper insertion of the aspirator 8 with the longitudinal axis 28 of the front face of the mouth 12 being parallel with the anterior (ventral) 46 and posterior (dorsal) 48 walls of the vagina 32 (FIG. 5).

A suction force to draw the cervico-vaginal fluid into passage 26 when the aspirator 8 is in position is created by the suction creating plunger indicated generally at 24. In its preferred embodiment shown in FIG. 2, the plunger 24 is composed of a shaft 14 movable within passage 26 and protruding therefrom. The shaft 14 has an inner end indicated generally at 44 which is closer to the mouth 12 and an outer end 42 which generally protrudes from the tube 10. On the inner end 44 of shaft 14 is a tip 18 desirably formed from a flexible rubbery material which fits tightly within passage 26. Movement of the tightly-fitting, flexible tip 18 from a first position at which the tip 18 abuts the mouth 12 to a second position along tube 10 creates a suction force drawing the cervico-vaginal fluid into passage 26. The tight fit of flexible tip 18 within the passage 26 also prevents the flow beyond the location of the tip 18 of the cervico-vaginal fluid drawn into passage 26.

A suction alleviating means 22 reduces the suction force caused by use of the aspirator thereby preventing tissue damage or pain due to pressure on the vaginal and cervical tissues by the suction force. In the preferred embodiment, shown in FIGS. 2 and 3, this suction alleviating means 22 is in the form of a narrow channel 22 extending along the length of the tube 10 on the exterior thereof, the channel 22 being separate and discrete from passage 26 and not communicative therewith. In the preferred position for sufficient suction alleviation, channel 22, upon insertion of aspirator 8, desirably faces the anterior wall 46 of the vagina 32.

FIG. 5 demonstrates the aspirator 8 of the present invention in its inserted position in the vagina 32. The mout 12 of the aspirator 8 lies in the posterior fornix 36 of the vagina 32 beneath the cervix 30. When the plunger 24 is moved from a position abutting the mouth 12 in a direction away from the mouth 12, a suction force is created which draws the cervico-vaginal fluid into the passage 26 of the aspirator 8. In this position, the aspirator 8 is able to obtain the maximal amount of cervico-vaginal fluid. Calibrations 20 along tube 10 enable the user to determine the volume of cervico-vaginal fluid upon withdrawal of the aspirator 8. Desirably the intervals of the calibrations 20 represent 50-microliter (0.05 ml) increments.

The method entails the reading of the volume of fluid obtained in the aspirator and the recording of said fluid volume, preferably every day of the cycle other than days of menstrual flow.

Figure 6:
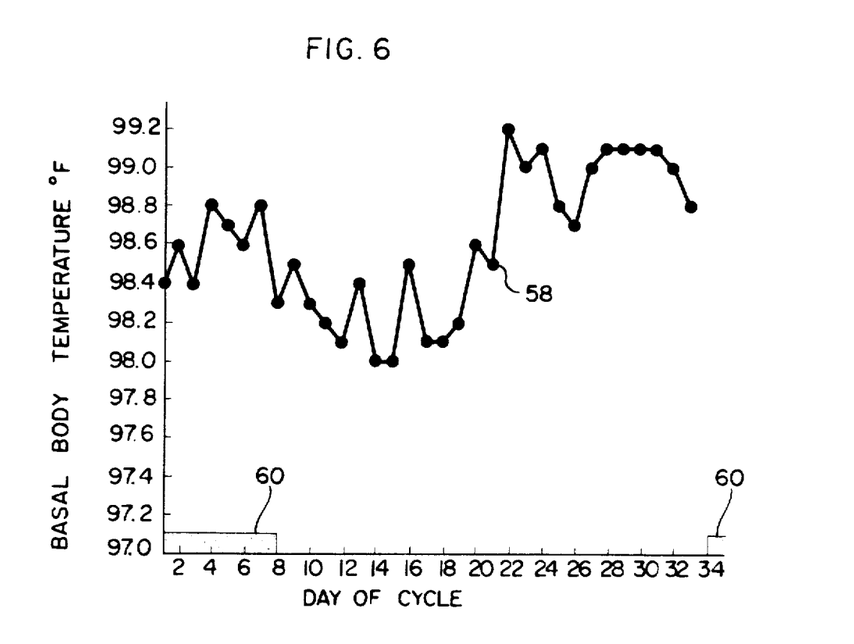
FIG. 6 is a graph of basal body temperature per day of cycle for one test subject using the method of the present invention.
Figure 7:
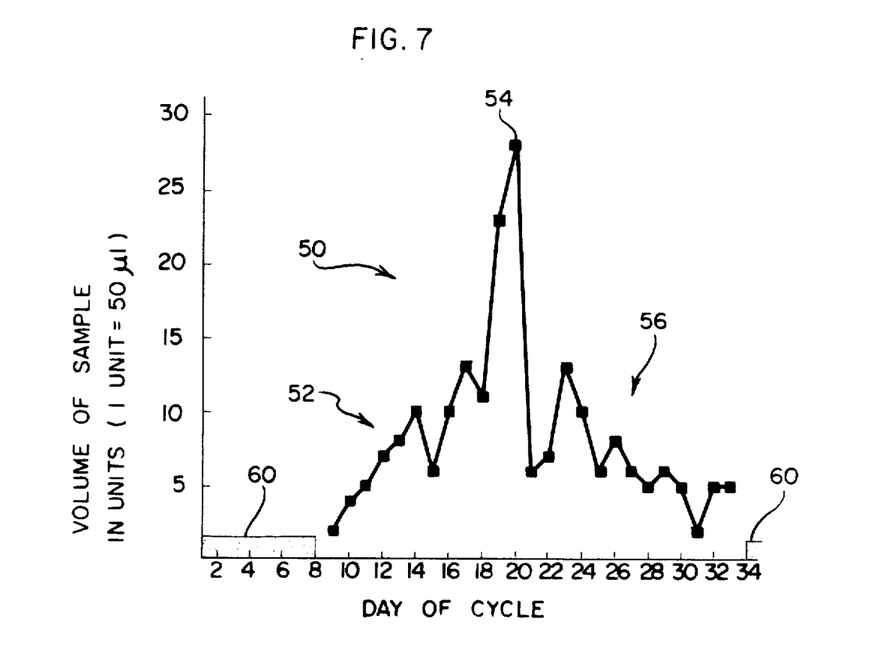
FIG. 7 is a graph of sample volume per day of cycle for the same subject and the same cycle as in FIG. 6.

The accuracy of this method in detecting ovulation is graphically demonstrated when the characteristic pattern indicated generally at 50 observed when one subject used the method and aspirator of the present invention (FIG. 7) is compared to the chart of basal body temperature taken on a per-day basis (FIG. 6) by the same subject during the same menstrual cycle. In both figures, indicated generally at 60 are days 34, and 1 through 8, the days of menses. In FIG. 7 no volume sample was collected on these days. From day nine to day 33 the subject used the aspirator of the present invention to record the sample volume of cervico-vaginal fluid obtained at roughly the same time every day. From day 9 to day 18, a slight increase 52 in cervico-vaginal fluid was observed; however, the average of these days was approximately 400 μl. Day 19 showed a significant increase which was also evident on day 20, indicating the immediate preovulatory, highly fertile period. Following the Volume Peak 54 which occurred at day 20, the amount of cervico-vaginal fluid decreased to a level at approximately day 24, indicative of the post-ovulatory or luteal phase base line volume 56, indicating infertility. Use of this method therefore indicated to the subject that her highly fertile period occurred most likely from day 19 to approximately day 22. The last day of low temperature 58, which in the method of basal body temperature indicates the day of presumptive ovulation, occurred on day 21, the day after the Volume Peak in FIG. 7.

Figure 8:
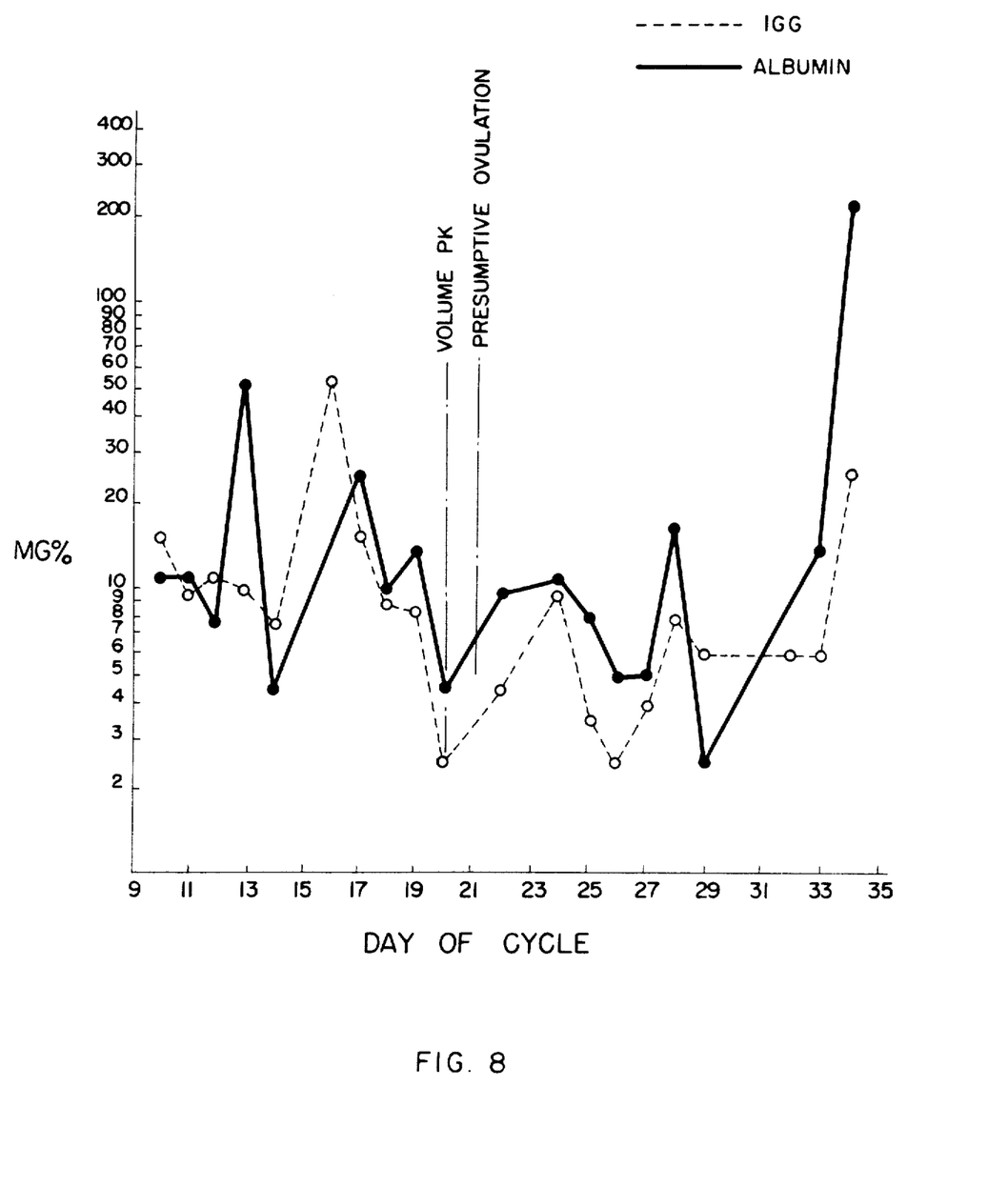
FIG. 8 is a logarithmic graph of concentration of immunoglobulin G and albumin in terms of milligrams per 100 milliliters (mg %) per day of cycle for the same subject and the same cycle graphed in FIGS. 6 and 7.

FIG. 8 is a logarithmic scale indicating the changes in the amounts of two constituents of cervico-vaginal fluid. The two constituents plotted are immunoglobulin G and albumin. Each of these constituents shows a definite decrease at the time of the Volume Peak. FIG. 8 correlates to the same cycle represented in FIGS. 6 and 7. The concentrations of IgG and albumin in vaginal fluid during the cycle establish a pattern which correlates with similar, though more concentrated values of these constituents when assayed in pure cervical mucus. Schumacher, G. B. F., "Humoral Immune Factors in the Female Reproductive Tract and Their Changes During the Cycle," *Immunological Aspects of Infertility and Fertility Regulation*, Dhindsa/Schumacher, eds. (Elsevier North Holland, Inc., 1980). Thus, another advantage of the present method is that it permits collection of cervico-vaginal fluid which may be stored for laboratory analyses where indicated, i.e., in work-ups on infertile couples.

The characteristic pattern of sample volume of cervico-vaginal fluid per day was repeated and correlated with basal body temperature in all of the subjects tested, in which infertile periods, both prior to and following the fertile period, are characterized by low average volumes. Impending ovulation is indicated in each case by a significant and very noticeable increase in sample volume of cervico-vaginal fluid, labelled the "Volume Peak." Volume Peak indicates that ovulation is occurring between the day of the Volume Peak to two days afterwards. When the volume of cervico-vaginal fluid returns to a low average, similar to that of the pre-ovulatory period, the subject has entered the luteal, infertile phase.

The following examples demonstrate the results of use of the method and apparatus in determining the onset of the ovulatory or fertile period.

EXAMPLE 1

A study of 7 healthy female volunteers between the ages of 19 and 33, representing investigation of 18 ovulatory menstrual cycles, was conducted.

All subjects obtained samples of cervico-vaginal secretions every morning at home via aspiration in accordance with the present invention. Daily samples were transferred to pre-weighed vials and sample weight was determined in the laboratory by the inventors. Sample weight as a function of day of cycle was analyzed in this investigation. However, sample weight can be considered equal to volume with a negligible error due to the only slightly higher mass density of cervico-vaginal secretions compared to water.

Along with daily sample collecting the subjects took morning BBT measurements. A few patients had a history of "mittelschmerz" at the time of ovulation and this was recorded when observed. Presumptive ovulation was assigned to the last day of low BBT and day of "mittelschmerz" where applicable.

The function of sample weight (volume) vs. day of cycle was consistent for all 18 cases. There was a pre-ovulatory baseline of sample size which in the early follicular phase was less than 100-200 mg (μ1), the average of the first four days after menses. In all cases there was a dramatic increase in sample volume 3-40 times the early preovulatory baseline levels near the time of ovulation, the Volume Peak. In 9 of 18 cycles the Volume Peak was greater than 6.0 times the preovulatory baseline and in 15 of 18 cycles greater than 4 times the preovulatory baseline. The minimum Volume Peak observed was 3 times the preovulatory baseline. The Volume Peak had a range of 300-1300 mg ($\mu$l) among the subjects.

Some subjects were producers of relatively low quantities of cervico-vaginal secretions and had Volume Peaks of approximately 300 mg ($\mu$l). Yet, their Volume Peaks were significantly above preovulatory baseline levels, making identification of the fertile phase a simple matter. For those women with low cervical mucus production the daily sampling method was extremely useful in identifying their fertile period. In this investigation the Volume Peak generally occurred 2 days (range 0-4 days) before presumptive ovulation. In the 18 cycles investigated, the Volume Peak occurred in 7 cycles two days before presumptive ovulation, in 7 cycles one day before presumptive ovulation, and in 3 cycles on the day of presumptive ovulation. The remaining cycle demonstrated an aberrant broad Volume Peak.

EXAMPLE 2

Subject E.K. utilized the method and apparatus of the present invention to detect her fertile period through five consecutive menstrual cycles. Table I shows her recordings of volume and laboratory measurements of weight of the cervico-vaginal fluid collected with the aspirator of the present invention and demonstrates a correlation with basal body temperature for cycles 2 through 5. In cycle 2, E.K. recorded only volume.

The results in Table I clearly demonstrate the ease in identifying the Volume Peak or Weight Peak of the recordings, which indicates the approximate onset of fertility and impending ovulation, in contrast to the low average sample volumes or weights of the preceding follicular and subsequent luteal phases. The Peak day correlates favorably with the BBT indications that ovulation *had* occurred sometime before the increase in temperature. From a comparison of the recordings for the present method and the BBT method, it is readily apparent that the volume of cervico-vaginal fluid increases significantly several days *before* the basal body temperature shift, and how much more accurate and easy to interpret are the volumetric and gravimetric recordings for detection and timing of ovulation.

TABLE I

| Day of Cycle | Cycle 2 Vol ($\mu$l) | Cycle 2 BBT (°F.) | Cycle 3 Vol ($\mu$l) | Cycle 3 Wt (mg) | Cycle 3 BBT (°F.) | Cycle 4 Vol ($\mu$l) | Cycle 4 Wt (mg) | Cycle 4 BBT (°F.) | Cycle 5 Vol ($\mu$l) | Cycle 5 Wt (mg) | Cycle 5 BBT (°F.) |
|---|---|---|---|---|---|---|---|---|---|---|---|
| 1 | | 98.4 | | | 98.6 | | | 98.5 | | | 98.6 |
| 2 | | 98.5 | | | 98.1 | | | 98.5 | | | 97.9 |
| 3 | | 98.4 | | | 98.7 | | | 98.5 | | | 97.9 |
| 4 | | 98.8 | | | 98.3 | | | 98.6 | | | 98.0 |
| 5 | | 98.7 | | | 98.4 | | | 97.9 | | | 98.2 |
| 6 | | 98.6 | | | 98.4 | | | 98.4 | | | 98.1 |
| 7 | | 98.8 | | | 98.7 | | | 98.6 | 100 | 100 | 98.6 |
| 8 | | 98.3 | 200 | 230 | 98.5 | 200 | 180 | 97.9 | 200 | 170 | 98.0 |
| 9 | 100 | 98.5 | 350 | 400 | 98.0 | 200 | 200 | 98.1 | 250 | 230 | 97.4 |
| 10 | 200 | 98.3 | 400 | 400 | 98.1 | 300 | 310 | 97.9 | 300 | 330 | 98.3 |
| 11 | 250 | 98.2 | 300 | 300 | 98.4 | 350 | 350 | 97.9 | 300 | 330 | 97.8 |
| 12 | 350 | 98.1 | 400 | 450 | 98.0 | 400 | 430 | 98.0 | 250 | 170 | 98.4 |
| 13 | 400 | 98.4 | 400 | 470 | 98.2 | 250 | 290 | 98.5 | 350 | 360 | 98.0 |
| 14 | 500 | 98.0 | 200 | 240 | 98.1 | 300 | 310 | 98.4 | 200 | 210 | 98.3 |
| 15 | 300 | 98.0 | 400 | 450 | 98.4 | 350 | 380 | 97.7 | 350 | 380 | 97.9 |
| 16 | 500 | 98.5 | 600 | 650 | 98.0 | 450 | 440 | 98.3 | 600 | 640 | 97.8 |
| 17 | 650 | 98.1 | 900 | 950 | 97.9 | 350 | 380 | 97.8 | 900 | 950 | 98.1 |
| 18 | 550 | 98.1 | 900 | 920 | 98.2 | 250 | 270 | 97.7 | 900 | 950 | 97.7 |
| 19 | 1150 | 98.2 | 1250 | 1250 | 98.2 | 1100 | 1020 | 97.7 | 1350 | 1290 | 98.4 |
| 20 | 1400 | 98.6 | 1450 | 1180 | 98.3 | 700 | 690 | 98.2 | 800 | 820 | 98.1 |
| 21 | 300 | 98.5 | 700 | 710 | 98.3 | 200 | 230 | 98.3 | 750 | 750 | 98.2 |
| 22 | 350 | 99.2 | 1200 | 960 | 98.5 | 350 | 360 | 98.5 | 500 | 630 | 98.6 |
| 23 | 650 | 99.0 | 650 | 680 | 98.3 | 350 | 380 | 98.5 | 300 | 360 | 98.6 |
| 24 | 500 | 99.1 | 400 | 450 | 98.4 | 200 | 250 | 98.8 | 500 | 540 | 99.2 |
| 25 | 300 | 98.8 | 400 | 530 | 98.8 | 250 | 270 | 98.6 | 450 | 480 | 98.8 |
| 26 | 400 | 98.7 | 350 | 370 | 98.9 | 100 | 120 | 98.8 | 450 | 490 | 99.0 |
| 27 | 300 | 99.0 | 250 | 300 | 98.9 | 200 | 220 | 99.0 | 450 | 470 | 99.1 |
| 28 | 250 | 99.1 | 300 | 320 | 98.9 | 250 | 280 | 99.1 | 200 | 240 | 99.1 |
| 29 | 300 | 99.1 | 200 | 220 | 98.8 | 200 | 210 | 98.8 | 250 | 300 | 99.1 |
| 30 | 250 | 99.1 | 650 | 410 | 99.2 | 200 | 230 | 99.0 | 300 | 320 | 98.8 |
| 31 | 100 | 99.1 | 250 | 300 | 99.2 | 250 | 250 | 99.0 | 250 | 310 | 98.9 |
| 32 | 250 | 99.0 | 200 | 230 | 99.0 | 200 | 190 | 98.8 | 400 | 450 | 98.9 |
| 33 | 250 | 98.8 | 250 | 260 | 99.0 | 200 | 190 | 98.6 | 200 | 240 | 98.8 |
| 34 | — | | 100 | 100 | 98.8 | 300 | 320 | 98.4 | 250 | 250 | 98.5 |
| 35 | — | | 300 | 320 | 99.1 | | | | 100 | 100 | 98.6 |
| 36 | | | 310 | 270 | 98.7 | | | | | | |

Patient EK - 4 cycles

The foregoing examples are provided for clarity of understanding only, without limiting the scope of the invention. Modifications to both method and apparatus will be obvious to those skilled in the art.

As one example, the suction-alleviating means, described in the preferred embodiment as a longitudinal channel, may be replaced by other embodiments such as a number of grooves spaced around the tube, shorter channels, or a concentrically-oriented channel.

Similarly, the method was described as enabling examination of the collected cervico-vaginal fluid for laboratory analysis of chemical components such as IgG or albumin. Other chemical constituents of the fluid may be analyzed. Also, an indicator to detect the presence or some quality of fluid constituents such as soluble proteins or pH, may be adhered to the interior of the tube as another mode of detecting chemical changes during the course of the menstrual cycle.

The method and apparatus may also be correlated with observable changes in the biological aspects of cervico-vaginal fluid. The invention enables observation of the consistency, color and translucency of each sample of cervico-vaginal fluid, so that changes in these parameters may also provide detectable information about the transitions between infertile to fertile phases. The noticeable increase in translucency and sliminess of cervico-vaginal fluid from early follicular to fertile phase can be observed, as well as the change from maximal translucency and sliminess to a whitish pastiness occurring during the transition from fertile phase to luteal, infertile phase.

What is claimed is:

1. A method of detecting the fertile and infertile phases in the human menstrual cycle comprising:
   daily collecting of cervico-vaginal fluid from the vagina over a period of days; and
   determining the cyclic pattern of volumetric changes in said fluid over said period of days to indicate the phases in the cycle.

2. The method recited in claim 1 wherein said collecting step comprises:
   collecting said cervico-vaginal fluid in a calibrated aspirator.

3. The method recited in claim 1 wherein said collecting step is performed at the same time every twenty-four hours.

4. The method recited in claim 1 and comprising:
   storing said cervico-vaginal fluid after said collecting and determining steps; and
   chemically analyzing said stored fluid.

5. The method recited in claim 4 and comprising:
   correlating the volumetric pattern of the cervico-vaginal fluid to cyclic changes in the chemical and biological constituents of the fluid.

6. The method recited in claims 4 or 5 wherein said analyzing step comprises analyzing for IgG and albumin.

7. A method of detecting the fertile and infertile phases in the human menstrual cycle comprising:
   daily collecting of cervico-vaginal fluid from the vagina over a period of days; and
   determining the cyclic pattern of gravimetric changes in said fluid over said period of days to indicate the phases in the cycle.

8. The method recited in claim 7 wherein said collecting step comprises:
   collecting said cervico-vaginal fluid in a calibrated aspirator.

9. The method recited in claim 7 wherein said collecting step is performed at the same time every twenty-four hours.

10. The method recited in claim 7 and further comprising:
    storing said cervico-vaginal fluid after said collecting and determining steps; and
    chemically analyzing said stored fluid.

11. The method recited in claim 10 and comprising:
    correlating the gravimetric pattern of the cervico-vaginal fluid to cyclic changes in the chemical and biological constituents of the fluid.

12. The method recited in claims 10 or 11 wherein said analyzing step comprises analyzing for IgG and albumin.

13. A method of detecting the fertile and infertile phases in the human menstrual cycle employing a series of steps performed once per day for at least several days preceding and following ovulation, said steps comprising:
    collecting cervico-vaginal fluid which naturally accumulates in the vagina during a normal daily interval;
    measuring and recording the volume of said collection of cervico-vaginal fluid; and
    determining from said recording the cyclic pattern of volumetric changes during a menstrual cycle;
    whereby the onset of the fertile phase and impending ovulation is indicated by an increase in volume in contrast to the low average volume of the infertile early follicular phase following menses and the infertile luteal phase, and
    whereby time of optimum fertility is indicated by a significant peak in volume, in contrast to the low average volume of the infertile early follicular phase following menses and the infertile luteal phase.

14. The method recited in claim 13 wherein said collecting step comprises:
    collecting said cervico-vaginal fluid in a calibrated aspirator.

15. The method recited in claim 13 wherein said collecting step is performed at the same time every twenty-four hours.

16. The method recited in claim 13 and comprising:
    storing said cervico-vaginal fluid after said collecting and determining steps; and
    chemically analyzing said stored fluid.

17. The method recited in claim 16 and comprising:
    correlating the volumetric pattern of the cervico-vaginal fluid to cyclic changes in the chemical and biological constituents of the fluid.

18. The method recited in claims 16 or 17 wherein said analyzing step comprises analyzing for IgG and albumin.

19. A method of detecting the fertile and the infertile phases in the human menstrual cycle employing a series of steps performed once per day for at least several days preceding and following ovulation, said steps comprising:
    collecting cervico-vaginal fluid which naturally accumulates in the vagina during a normal daily interval;
    measuring and recording the weight of such collection of cervico-vaginal fluid; and
    determining from said recording the cyclic pattern of gravimetric changes during the menstrual cycle;
    whereby the onset of the fertile phase and impending ovulation is indicated by an increase in weight in contrast to the low average weight of the infertile early follicular phase following menses and the infertile luteal phase, and
    whereby the time of optimum fertility is indicated by a significant peak in volume in contrast to the low average weight of the infertile early follicular phase following menses and the infertile luteal phase.

20. The method recited in claim 19 wherein said collecting step comprises:
    collecting said cervico-vaginal fluid in a calibrated aspirator.

21. The method recited in claim 19 wherein said collecting step is performed at the same time every twenty-four hours.

22. The method recited in claim 19 and comprising:
storing said cervico-vaginal fluid after said collecting and determining steps; and
chemically analyzing said stored fluid.

23. The method recited in claim 22 and comprising:
correlating the gravimetric pattern of the cervico-vaginal fluid to cyclic changes in the chemical and biological constituents of the fluid.

24. The method recited in claims 22 or 23 wherein said analyzing step comprises analyzing for IgG and albumin.

25. An apparatus for collection of total cervico-vaginal fluid from a vaginal cavity having a vaginal wall and a cervix located at its upper end, said apparatus being adaptable for self-use by a female subject and comprising:
elongated, cylindrical tube means having a continuous longitudinal passage therethrough and an exterior surface, for insertion into a vaginal cavity;
mouth means positioned at one end of said tube means for receiving cervico-vaginal fluid, said mouth means comprising means for preventing traumatization or perforation of the tissue of the vaginal wall or the cervix when said mouth means is in a predetermined orientation and means for easing said mouth means into the posterior fornix of said vaginal cavity;
means on another end of said tube means, opposite said mouth means, for maintaining said mouth means in said predetermined orientation when said mouth means is inside said vaginal cavity; and
means for creating a suction force inside said passage to aspirate said cervico-vaginal fluid into said passage of said tube means when said apparatus is in said vaginal cavity.

26. An apparatus as recited in claim 25 and comprising:
means on said tube means for alleviating said suction force, upon aspiration of said fluid from the vaginal cavity, thereby preventing tissue damage or pain due to pressure created by said suction force.

27. The apparatus recited in claim 26 wherein said means for alleviating said suction force comprises:
a channel extending along the length of said tube means on the exterior surface thereof, said channel being separate and discrete from said longitudinal passage in said tube means and being non-communicative therewith.

28. The apparatus recited in claim 25 and comprising:
indicator means within said passage for detecting the chemical properties of said cervico-vaginal fluid.

29. The apparatus recited in claim 25 wherein the exterior surface of said tube means comprises volumetric calibrations along its entire length.

30. The apparatus recited in claim 25 wherein said maintaining means is substantially rectangular.

31. The apparatus recited in claim 25 wherein said mouth means is bulbously enlarged and elliptically shaped 32. The apparatus recited in claim 25 wherein:
said maintaining means comprises means for monitoring the proper positioning of said mouth means in said predetermined orientation.

33. The apparatus recited in claim 25 wherein:
said maintaining means is substantially rectangular; and
said mouth means is bulbously enlarged and elliptically shaped.

34. The apparatus recited in claim 33 wherein:
said rectangular maintaining means is oriented with its longest side parallel to the longitudinal axis of said elliptical mouth means and comprises means for monitoring proper positioning of said mouth means in said predetermined orientation by observation of the orientation of said rectangular maintaining means.

35. The apparatus recited in claim 25 wherein said suction-creating means comprises:
a shaft reciprocally movable within said passage;
said shaft having an inner end and an outer end, said inner end being located closer to said mouth means than said outer end; and
a tip located on said inner end of said shaft, said tip comprising means for preventing the flow beyond the location of said tip of cervico-vaginal fluid drawn into said passage.

36. An apparatus for collection of cervico-vaginal fluid from a vaginal cavity having a vaginal wall and a cervix located at its upper end, said apparatus being adaptable for self-use by a female subject and comprising:
elongated, cylindrical tube means having a continuous longitudinal passage therethrough and an exterior surface for insertion into a vaginal cavity;
mouth means positioned at one end of said tube means for receiving cervico-vaginal fluid;
means for creating a suction force inside said passage to aspirate said cervico-vaginal fluid into said passage of said tube means when said apparatus is in said vaginal cavity; and
means on said tube means for alleviating said suction force, upon aspiration of said fluid from the vaginal cavity, thereby preventing tissue damage or pain due to pressure created by said suction force.

37. The apparatus recited in claim 36 and comprising:
indicator means within said passage for detecting the chemical properties of said cervico-vaginal fluid.

38. The apparatus recited in claim 36 wherein the exterior surface of said tube means comprises volumetric calibrations along its entire length.

39. The apparatus recited in claim 36 wherein said mouth means is bulbously enlarged and elliptically shaped.

40. The apparatus recited in claim 36 wherein said means for alleviating said suction force comprises:
a channel extending along the length of said tube means on the exterior surface thereof, said channel being separate and discrete from said longitudinal passage in said tube means and being non-communicative therewith.

41. The apparatus recited in claim 36 wherein said suction-creating means comprises:
shaft reciprocally movable within said passage;
said shaft means having an inner end and an outer end, said inner end being located closer to said mouth means than said outer end; and
a tip located on said inner end of said shaft, said tip comprising means for preventing the flow beyond the location of said tip of cervico-vaginal fluid drawn into said passage.

* * * * *